(12) United States Patent
Buijsse et al.

(10) Patent No.: US 10,545,100 B2
(45) Date of Patent: Jan. 28, 2020

(54) X-RAY IMAGING TECHNIQUE

(71) Applicant: FEI Company, Hillsboro, OR (US)

(72) Inventors: Bart Buijsse, Eindhoven (NL); Faysal Boughorbel, Eindhoven (NL)

(73) Assignee: FEI Company

(*) Notice: Subject to any disclaimer, the term of this patent is extended or adjusted under 35 U.S.C. 154(b) by 400 days.

(21) Appl. No.: 15/264,132

(22) Filed: Sep. 13, 2016

(65) Prior Publication Data
US 2017/0138870 A1    May 18, 2017

(30) Foreign Application Priority Data
Nov. 18, 2015    (EP) .................................... 15195079

(51) Int. Cl.
*G01N 23/04* (2018.01)
*H01J 35/00* (2006.01)
*H01J 37/28* (2006.01)

(52) U.S. Cl.
CPC .............. *G01N 23/04* (2013.01); *H01J 37/28* (2013.01)

(58) Field of Classification Search
CPC ....... A61B 6/032; A61B 6/037; A61B 6/5282; A61B 6/027; A61B 6/488; A61B 6/5211; A61B 6/4233; A61B 6/4291; A61B 6/4441; A61B 6/466; A61B 6/507; A61B 6/5258; A61B 6/5294; A61B 6/40; A61B 6/5205; A61B 90/11; A61B 90/36; A61B 10/0233; A61B 17/3403; A61B 18/18; A61B 2090/363; A61B 2090/3966; A61B 5/1075; A61B 6/12; A61B 6/504; A61B 6/505; G06T 11/005; G06T 2207/10116; G06T 11/008; G06T 11/60; H01J 37/28; H01J 37/222; H01J 2237/226; H01J 37/261; H01J 2237/206; H01J 2237/208; H01J 2237/221; H01J 2237/31745; H01J 37/26; H01J 2237/0453; H01J 2237/216; H01J 2237/2802; H01J 37/21; H01J 37/244;
(Continued)

(56) References Cited

U.S. PATENT DOCUMENTS

| | | | |
|---|---|---|---|
| 9,390,881 B2* | 7/2016 | Yun | ......................... G21K 1/06 |
| 2009/0185660 A1* | 7/2009 | Zou | ....................... H01J 1/3048 |
| | | | 378/122 |

(Continued)

FOREIGN PATENT DOCUMENTS

| | | |
|---|---|---|
| EP | 2648208 A2 | 10/2013 |
| WO | 2010109401 A1 | 9/2010 |
| WO | 2010150136 A1 | 12/2010 |

OTHER PUBLICATIONS

"Transmission Electron Microscopy", Wikipedia, Retrieved from the Internet Jul. 25, 2016, http://en.wikipedia.org/wiki/Transmission_electron_microscopy, 23 pages.
(Continued)

*Primary Examiner* — Irakli Kiknadze

(57) ABSTRACT

An x-ray source for computer tomography uses several sub-sources. An electron beam impacts the several sub-sources to achieve a high x-ray flux with high resolution. The several sub-sources produce a composite image, which is deconvolved to disentangle the composite image and render a useful image. The configuration of the several sub-sources can be optimized for a given specimen structure.

19 Claims, 8 Drawing Sheets

(58) Field of Classification Search
CPC .............. H01J 37/263; H01J 2235/068; H01J 2235/086; H01J 35/08; H01J 2235/081; H01J 35/14; H01J 35/18; H01J 2235/1204; H01J 35/10; H01J 35/12; H01J 35/26; H01J 2235/088; H01J 2235/1291; H01J 35/105; H01J 35/108; H01J 35/30; H01J 35/02; H01J 35/025; H01J 35/106; H01J 35/116; H01J 35/06; H01J 35/32; H01J 2235/062; H01J 35/04; H01J 35/16; H01J 2235/166; H01J 2201/304; G01N 2223/401; G01N 23/225; G01N 2223/423; G01N 1/06; G01N 1/36; G01N 2223/418; G01N 23/22; G01N 2021/6439; G01N 21/6428; G01N 21/6456; G01N 21/6458; G01N 21/6486; G01N 21/64; G01N 2223/079; G01N 2223/08; G01N 2223/02; G01N 2223/204; G01N 2223/419; G01N 23/04; G01N 23/20075; G01N 2223/612
USPC .................... 378/4, 19, 43, 62, 79, 122, 143
See application file for complete search history.

(56) References Cited

U.S. PATENT DOCUMENTS

| | | | | |
|---|---|---|---|---|
| 2009/0316860 | A1* | 12/2009 | Okunuki | H01J 35/065 378/122 |
| 2011/0170663 | A1* | 7/2011 | Boese | A61B 6/4233 378/62 |
| 2015/0071402 | A1 | 3/2015 | Handa | |
| 2015/0228440 | A1 | 8/2015 | Hwu et al. | |
| 2015/0279615 | A1 | 10/2015 | Potocek et al. | |
| 2015/0371815 | A1 | 12/2015 | Potocek et al. | |
| 2016/0013015 | A1 | 1/2016 | Potocek et al. | |
| 2016/0111247 | A1 | 4/2016 | Potocek et al. | |

OTHER PUBLICATIONS

"X-Ray Microtomography", Wikipedia, Retrieved from the Internet Aug. 4, 2016, https://en.wikipedia.org/wiki/X-ray_microtomography, 5 pages.
Cichocki, A., et al. "Families of Alpha-Beta-and Gamma-Divergences: Flexible and Robust Measures of Similarities", Entropy, Jan. 14, 2010, pp. 1532-1568, vol. 12 Issue 6.
Cichocki, A., et al. "Generalized Alpha-Beta Divergences and Their Application to Robust Nonnegative Matrix Factorization", Entropy, Jan. 14, 2011, pp. 137-170, vol. 13 Issue 1.
Escovitz, W.H. et al., "Scanning Transmission Ion Microscope with a Field Ion Source," Proc. Nat. Acad. Sci. USA, May 1975, pp. 1826-1828, vol. 72, No. 5.
Levin, A., et al. "Image and depth from a conventional camera with a coded aperture", ACM Transactions on Graphics, Jul. 29, 2007, 9 pages, vol. 26 Issue 3.
Neuser, E., et al. "NanoCT® Visualizing internal 3D structures with submicrometer resolution", DIR 2007, 18 p, vol. 39 Issue 41,International symposium on digital industrial radiology and computed tomography, France.
Varentsov, D. et al. "First biological images with high-energy proton microscopy", Physica Medica (2013), pp. 208-213, vol. 29.
"Bhattacharyya Distance", Wikipedia, Retrieved from the Internet Nov. 7, 2016, http://en.wikipedia.org/wiki/Bhattacharyya_distance, 4 pages.
"Bregman Divergence", Wikipedia, Retrieved from the Internet Nov. 7, 2016, http://en.wikipedia.org/wiki/Bregman_divergence, 4 pages.
"Cone Beam Computed Tomography", Wikipedia, Retrieved from the Internet Aug. 4, 2016, https://en.wikipedia.org/wiki/Cone_beam_computed_tomography, 8 pages.
"Cramer-Rao Bound", Wikipedia, Retrieved from the Internet Nov. 7, 2016, http://en.wikipedia.org/wiki/Cramer-Rao_bound, 7 pages.
"Electron Microscope", Wikipedia, Retrieved from the Internet Oct. 15, 2015, http://en.wikipedia.org/wiki/Electron_microscope, 11 pages.
"F-Divergence", Wikipedia, Retrieved from the Internet Nov. 7, 2016, http://en.wikipedia.org/wiki/F-divergence, 3 pages.
"Focused Ion Beam", Wikipedia, Retrieved from the Internet Jul. 11, 2016, https://en.wikipedia.org/wiki/Focused_ion_beam, 7 pages.
"Iteratively Reweighted Least Squares", Wikipedia, Retrieved from the Internet Nov. 7, 2016, https://en.wikipedia.org/wiki/Iteratively_reweighted_least_squares, 3 pages.
"Kullback-Leibler Divergence," Wikipedia, Retrieved from the Internet Nov. 9, 2012; http://en.wikipedia.org/wiki/Kullback%E2%80%93Leibler_divergence, 14 pages.
"Least Squares", Wikipedia, Retrieved from the Internet Nov. 7, 2016, http://en.wikipedia.org/wiki/Least_squares, 11 pages.
"Nanotomography", Wikipedia, Retrieved from the Internet Aug. 4, 2016, from https://en.wikipedia.org/wiki/Nanotomography, 1 page.
"Scanning Electron Microscope", Wikipedia. Retrieved from the Internet Jul. 25, 2016, http://en.wikipedia.org/wiki/Scanning_electron_microscope, 23 pages.
"Scanning Helium Ion Microscope", Wikipedia, Retrieved from the Internet on Jul. 25, 2016, http://en.wikipedia.org/wiki/Scanning_Helium_Ion_Microscope, 2 pages.
"Scanning Transmission Electron Microscopy", Wikipedia, Retrieved from the Internet Jul. 25, 2016, http://en.wikipedia.org/wiki/Scanning_transmission_electron_microscopy, 5 pages.
"Spiral Computed Tomography", Wikipedia, Retrieved from the Internet Aug. 4, 2016, https://en.wikipedia.org/wiki/Spiral_computed_tomography, 2 pages.

* cited by examiner

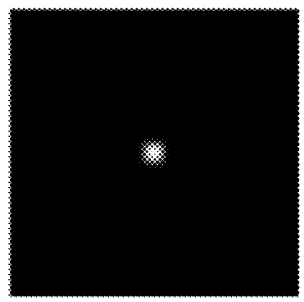
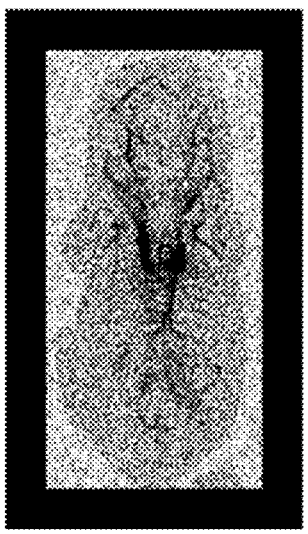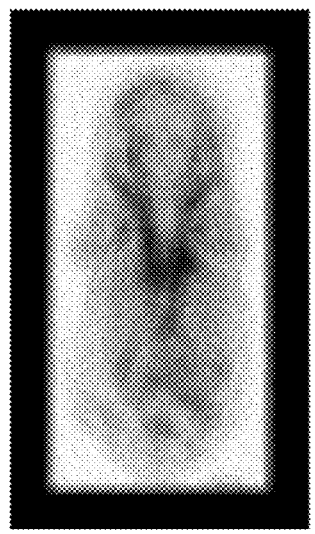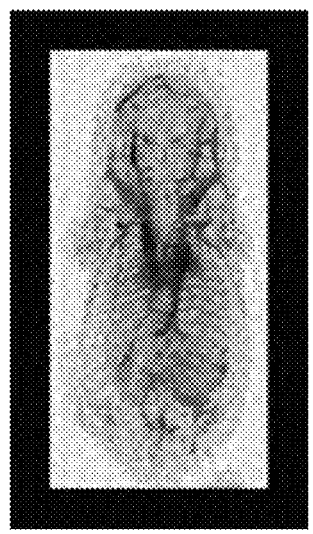
Fig. 4A  Fig. 4B  Fig. 4C

X-RAY IMAGING TECHNIQUE

The invention relates to a method of imaging a specimen using an X-ray imaging apparatus, comprising the following steps:
  Providing the specimen on a specimen holder;
  Directing a flux of X-rays from a source through the specimen and onto an X-ray camera.

The invention also relates to an X-ray imaging apparatus that can be used in performing such a method.

The invention further relates to a charged-particle microscope provided with such an X-ray imaging apparatus.

X-ray imaging has various important applications in, for example, medical science, forensics, metallurgy/materials science, structural performance/integrity studies, geology/petrology, lithography, security screening, etc. Traditionally, the employed X-ray source generates Bremsstrahlung (and characteristic/element-specific) X-rays by bombarding a metal source with a high-energy electron beam. These X-rays are directed so as to traverse the specimen in question (which may, for example, be a portion of a larger body) and then land on an X-ray imaging device (camera, detector) such as a CCD image sensor, for instance. The image thus registered will in many situations be used "as is"; however, in other situations, a collection of such images will be acquired along different lines of sight relative to the specimen, and these will then be used to construct an X-ray tomogram.

In tomographic imaging (also referred to as Computed Tomography (CT)), there are various ways to achieve a series of different lines of sight as alluded to above. For example, one can choose to:
  (a) Keep the source and detector static and move the specimen relative to them;
  (b) Keep the specimen static and move the source relative to it. In this case, one can elect to:
    Move the detector in synchronization with the source; or
    Embody the detector as a (static) array of sub-detectors, with positions matched to correspond to the different positions to be assumed by the source.

Regardless of whether the source or specimen is moved, it is possible to describe their relative motion using (for example) a specimen-centric coordinate system/reference frame. The flux of radiation that traverses the specimen can, for example, be regarded as being cone-like (thus yielding so-called cone beam tomography) or resembling a segment of a disc (thus yielding so-called fan beam tomography), depending on the geometry/shape that the detector "presents" to the source; a parallel/collimated flux is also possible.

As regards the specimen/source relative motion employed to achieve different lines of sight [data acquisition step], use is conventionally made of:
  A circular scan, in which the source follows a planar orbit about the specimen, and images are captured at a relatively high sampling rate (i.e. quasi-continuously) along this orbit. This type of scan can be applied in situations where only a relatively thin "slice" of a specimen has to be imaged, e.g. when making a cone beam CT scan of human dentition.
  See, for example, the following reference:
    wikipedia.org/wiki/Cone_beam_computed_tomography
  A helical scan, in which the source follows a coil-like (spiral) path about a (longitudinal) axis of the specimen, and images are again captured at a relatively high sampling rate (i.e. quasi-continuously) along this path. This type of scan can be applied in situations where a relatively elongated portion of a specimen has to be imaged, e.g. when making a CT scan of (a portion of) a human vertebral column. It is typically achieved by combining circular motion (e.g. of the source) and concurrent translational motion (e.g. of the specimen).
  See, for example, the following reference:
    wikipedia.org/wiki/Spiral_computed_tomography
  As an alternative to conventional curvilinear scan loci—such as the circular/spiral scan paths just referred to—one can, for example, also make use of a lattice-like data acquisition locus, e.g. as set forth in co-pending European Patent Application EP15181202.1 (FNL1515).

The "raw" imaging data obtained in the data acquisition step can subsequently be used as a basis for tomogram construction [data processing step]. For example:
  A common technique used in tomographic reconstruction is so-called Back Projection (BP). BP is a procedure whereby an image of a specimen, taken along a given line of sight, is back-projected (smeared out) along that line of sight, through the specimen. When this is done for several appropriately chosen lines of sight, the various back-projected images will intersect and form a blurry image at the location of the specimen, which blurry image then forms a basis for subsequent processing. This basic BP technique can, if desired, be modified by applying appropriate filtering to the image data prior to back-projection [Filtered Back Projection (FBP)] or after back-projection [Back Projection Filtering (BPF)].
  As an alternative and/or supplement to the use of BP, one can instead make use of an iterative reconstruction technique to produce a tomographic image. Examples of such iterative techniques include SIRT (Simultaneous Iterative Reconstruction Technique), ART (Algebraic Reconstruction Technique), DART (Discrete ART), SART (Simultaneous ART), etc. Such iterative techniques (generally) have the advantage of being less noise-sensitive, and of allowing (physical) constraints to be applied to the reconstruction process; however, because they employ several iterations, they tend to be more time-consuming, and to converge relatively slowly.

Tomographic imaging as referred to here can be performed using a standalone apparatus, which is conventionally the case in medical imaging applications, for example, where the specimen (e.g. a human or animal) is macroscopic. Standalone CT tools are also available for performing so-called "micro CT", in which a micro-focused source is used to image microscopic specimens, e.g. in geology/petrology, biological tissue studies, etc. Continuing this drive toward ever-greater resolution, so-called "nano CT" instruments have also been developed; these may be standalone tools, but, for example, they may also be embodied as (add-on) modules for (a vacant vacuum/interface port of) a charged-particle microscope (CPM), in which case the CPM's charged-particle beam can be used to irradiate a metal target, causing production of Bremsstrahlung (and characteristic) X-rays that are then used to perform the desired tomography (see FIG. 6B, for example). More information on (some) of these topics can, for example, be gleaned from the following references:
  wikipedia.org/wiki/X-ray_microtomography
  wikipedia.org/wiki/Nanotomography
  www.ndt.net/article/dir2007/papers/24.pdf It should be noted that, as referred to here in the context of a CPM, the phrase "charged particle" should be broadly construed as encompassing:

Electrons, as in the case of a Transmission Electron Microscope (TEM), Scanning Electron Microscope (SEM), and Scanning Transmission Electron Microscope (STEM), for instance. See, for example, the following references:
wikipedia.org/wiki/Electron_microscope
wikipedia.org/wiki/Scanning_electron_microscope
wikipedia.org/wiki/Transmission_electron_microscopy
wikipedia.org/wiki/Scanning_transmission_electron_microscopy Ions, which may be positive (e.g. Ga or He ions) or negative. Such ion beams can be used for imaging purposes, but they are also often used for surface modification purposes, e.g. as in the case of Focused Ion Beam (FIB) milling, Ion-Beam-Induced Deposition (IBID), Ion-Beam-Induced Etching (IBIE), etc. See, for example, the following references:
wikipedia.org/wiki/Focused_ion_beam
wikipedia.org/wiki/Scanning_Helium_Ion_Microscope
W. H. Escovitz, T. R. Fox and R. Levi-Setti, *Scanning Transmission Ion Microscope with a Field Ion Source*, Proc. Nat. Acad. Sci. USA 72(5), pp 1826-1828 (1975).

Other charged particles, such as protons and positrons, for instance. See, for example, the following reference:
www.ncbi.nlm.nih.gov/pubmed/22472444

It should also be noted that, in addition to imaging and/or surface modification, a charged particle beam in a CPM may also have other functionalities, such as performing spectroscopy, examining diffractograms, etc.

Although known X-ray imaging methods/apparatus produce tolerable imaging results, there is always room for improvement. In that context, the current inventors have worked extensively to identify shortcomings in conventional X-ray imaging approaches, and to address these effectively so as to produce improved performance. The results of such endeavor are the subject of the current application.

It is an object of the invention to provide an innovative X-ray imaging method/apparatus. More specifically, it is an object of the invention that this technique should employ a radically different illumination strategy as compared to known techniques.

These and other objects are achieved in a method as set forth in the opening paragraph above, which method is characterized by the following steps:

Embodying the source as a cluster of component sources (sub-sources), which cluster has a confined angular span relative to the specimen;
Using said camera to record a cumulative, composite image from said component sources;
Mathematically deconvolving said composite image.

The invention achieves various different advantages—both physical and mathematical in nature—which can be set forth as follows:

(i) In order to achieve fast imaging—with sufficient signal-to-noise ratio (SNR)/contrast-to-noise ratio (CNR)—one would like to employ a high X-ray flux, since this will deliver a relatively large X-ray dose in a relatively short time span. This is of particular importance in tomographic imaging, where a large number (e.g. hundreds) of individual images has to be acquired (for input into the tomogram reconstruction process), and where a given throughput penalty per image will ultimately add up to a relatively severe cumulative imaging delay. To address this problem and achieve higher X-ray flux, one might consider increasing the beam current of the bombarding electron beam in the X-ray source; however, such an increase will eventually run up against a thermal limit, since an excessively high beam current will ultimately cause the bombarded metal target to start melting. This problem is exacerbated in the case of the relatively small metal targets used in micro CT and nano CT, where the limited target volume constrains the available total current. The invention addresses this problem by providing the opportunity to simultaneously use the X-ray flux from several sub-sources (component sources) at once; in this way, the beam current per source can be kept (just) low enough to prevent source melting, and higher flux is instead achieved using source multiplicity. The obvious problem with this approach is that the composite (integrated) image thus registered by the detector will be a "blurred mess" of (only partially overlapping) individual images from each of the component sources—something which would normally render such an approach unviable. However, the current invention solves this problem by using innovative mathematical deconvolution techniques to "disentangle" the composite image, and render it just as usable as a conventional, single-source image.

(ii) By working with a cluster of component sources instead of a single source, the inventive method introduces new variables, which can be tuned for image optimization purposes. In particular, the invention opens the way to optimize the source configuration (number/spatial distribution/angular spread of component sources) to match a given specimen type/structure. For example:

When imaging semiconductor specimens with regular linear structures, it becomes possible (if desired) to employ different source configurations to image "dense grid" and "isolated line" geometries. It similarly becomes possible to use different source configurations to image "45-degree" lines and "orthogonal lines", for instance.

When imaging a repetitive structure—such as a grating or array, for instance—the source configuration can be chosen so as to suppress or enhance certain frequencies in the specimen's Fourier spectrum.

(iii) The inventive component sources do not have to be "fired" simultaneously, but can instead be fired sequentially. Sequential firing of component sources introduces advantages as regards thermal load, since a source that is briefly fired will have different thermal constraints to one that is (semi-)continuously "on". Moreover, this approach allows imaging to be performed by successively firing different (sparse) subsets of component sources, producing images that can subsequently be subjected to an averaging procedure to mitigate noise effects; for example, the inventors have shown that, under certain circumstances, a sharper final image can be achieved using a succession of 7 different source configurations—each with 7 component sources—than can be achieved in a single imaging session with 49 (=7×7) component sources. As regards implementation:

With reference to a first type of embodiment described below: such sequential firing can, for example, be achieved by using a tightly focused charged-particle beam (rather than a relatively broad beam) to bombard metallic targets (component sources) one-at-a-time rather than en masse, and "stepping" (or "swiping") the beam from one target to another, as desired. In such a scenario, one can achieve a reduction in background signal, since a narrower bombarding beam will irradiate less non-target material than a broad beam. One can also potentially achieve a higher current density (and, thus, higher associated X-ray flux) with a more-focused bombarding beam.

With regard to a second type of embodiment discussed below: one can simply fire component FEGs in an array sequentially rather than simultaneously.

These and other advantages will receive further elucidation below.

In a particular embodiment of the invention, said deconvolution is performed using an iterative re-weighted convergence technique employing a Point Spread Function kernel for said cluster of component sources. In this regard, the following deserves mention:

(I) Examples of Iterative Re-weighted Convergence (IRC) techniques include, for example, iterative re-weighted least-squares (IRLS) optimization, iterative re-weighted/l minimization, etc. See, for example the following reference:

wikipedia.org/wiki/Iteratively_reweighted_least_squares

Considered in general terms, such techniques seek to iteratively minimize a chosen divergence criterion. In this regard, many different divergence criteria can be chosen, depending on the particulars of a given situation (e.g. a particular noise model employed, such as Gaussian or Poisson). Examples include Least Squares Distance, Csiszar-Morimoto F-divergences, Bregman Divergences, Alpha-Beta-Divergences, the Bhattacharyya Distance, the Cramér-Rao Bound, and derivatives/combinations of these.

With regard to these broad divergence classes, the following can be noted:

Csiszar-Morimoto F-divergences (and derived measures) include the I and J Kullback-Leibler divergences, the Total Variation, Harmonic Mean, and Chi-Square measures, as well as several other entropy-based measures. See, for example:
wikipedia.org/wiki/F-divergence.

Bregman Divergences (and derived measures) include inter alia the Mahalonobis distance. See, for example:
wikipedia.org/wiki/Bregman_divergence Alpha-Beta-Divergences (and derived measures) include measures such as the generalized Kullback-Leibler, Triangular Discrimination, and Arithmetic Geometric measures. See, for example:

Cichocki, A; Cruces, S; Amari, S., *Generalized Alpha-Beta Divergences and Their Application to Robust Nonnegative Matrix Factorization*, Entropy 13, 134-170 (2011).

Cichocki, A; Amari, S, *Families of Alpha-Beta-and Gamma-Divergences: Flexible and Robust Measures of Similarities*, Entropy, 12, 1532-1568 (2010).

The Bhattacharyya Distance measures the similarity of two discrete or continuous probability distributions. See, for example:
wikipedia.org/wiki/Bhattacharyya_distance For additional information, see, for example:
wikipedia.org/wiki/Least_squares
wikipedia.org/wiki/Kullback-Leibler_divergence wikipedia.org/wiki/Cramer-Rao_bound (II) The Point Spread Function (PSF) kernel can, for example, be determined by recording a camera image of the employed cluster of component sources in the presence of a test specimen comprising a feature that emulates a Dirac delta function—such as a small hole, or a small absorbing body (e.g. gold sphere), for instance; this essentially produces a "pinhole image" of the kernel. Alternatively, it may be calculated/modeled for a given cluster configuration, e.g. using a Monte Carlo method. Yet another possible approach is to just image the source using a SEM (e.g. in backscatter mode). Such steps can be performed before or after (or during) specimen imaging with the cluster in question.

(III) If desired, the IRC technique can be regularized by incorporating into the optimization process an extra (additive) term that is a function of image gradient.

For a further elucidation of these points, see (for example) Embodiment 7 below.

In a particular embodiment of the current invention, the distribution of component sources is non-regular, i.e. the cluster of sub-sources in the inventive source has a geometrically non-regular arrangement. As opposed to a regular distribution—in which the component sources are arranged on (the nodes of) a regular "grid", such as an orthogonal, hexagonal or nested-circular grid, for instance—the component sources in the present arrangement cannot be fitted to a strict grid; as a result, the associated Fourier spectrum will tend to be "flatter", as opposed to being dominated by the characteristic frequencies associated with a regular grid. This effect becomes more pronounced as the distribution becomes more irregular, and is optimum for a random/pseudo-random distribution. Such a "Fourier space-filling" arrangement can be of particular benefit when imaging substantially "homogeneous" specimens, such as biological tissue or grained mineralogical matrix, for example.

As regards the size (angular extent) of the inventive cluster of sub-sources, the following considerations deserve mention. Consider a smallest circle that just encapsulates a given cluster configuration, and whose plane is substantially normal to an axis extending from a barycenter Cs of the specimen toward a barycenter Cc of the cluster. The diameter of this circle is W, and this will subtend a given (planar) "opening angle" $\theta$ at Cs, with a value dependent on the distance L from Cs to Cc. If W is relatively small relative to L, then $\theta \sim W/2L$ (radians) or $(180/\pi) \times W/2L$ (degrees). In the current invention, the angular span (distribution, extent) of the cluster of component sources is "confined" in that $\theta << 180°$, so that the cluster only occupies a relatively (very) small area of a hemisphere of radius L centered on Cs. For example, one can choose an angular distribution/cluster size that satisfies $\theta < 10°$, preferably $\theta < 5°$, and even more preferably $\theta < 1°$. In a specific set-up, for instance, the inventors used $W \approx 2$ µm and $L \approx 200$ µm, resulting in $\theta \approx 0.3°$. A tendency seen by the inventors in various experiments was that, in the current invention, the resolution of the deconvolved image tends to be better when using relatively confined/compact clusters (i.e. relatively small $\theta$ values).

In an exemplary embodiment of the present invention, the following applies:

The source comprises a body of supporting material in which the component sources are suspended as discrete metallic bodies;

Component sources are caused to emit X-rays by irradiating them with a charged-particle beam.

The body of supporting material may, for example, comprise a block or sheet/film of "low-Z" (low atomic number) material, and will preferably have a relatively good thermal conductivity; examples of such materials include Be, B, C, Al, etc. The metallic bodies (anodes) suspended/distributed in the supporting material will preferably comprise "high-Z" (high atomic number) material, such as Au, Cu, Mo, etc. These bodies can, for instance, take the form of small metal balls, cubes or cylinders (or other "pellet-like" shapes), e.g. with a size (diameter) of the order of about 75-125 nm. The charged-particle beam directed at such a source may, for example, have a footprint that is:

Relatively broad, so as to bombard several of the component sources at once (simultaneous firing); or Relatively narrow (tightly focused), so as to bombard only one component source at a time, but steerable so as to allow the beam to be sequentially directed onto a succession of different component sources (sequential firing).

The distribution of component sources within the supporting material may be chosen to have a desired geometry/configuration (e.g. random, or regular), characteristic spacing (the average distance between neighboring component sources), overall size (which will determine the angular extent/span presented to the specimen) and composition (particular choice of material composition); for example, the metallic bodies may be spheroids of average diameter d≈100 nm and composed of Au (gold), which are (quasi-)randomly distributed in a (planar) film of C (carbon) with an average (neighboring) separation ~d, and irradiated with an electron beam that is broad enough to bombard 20-25 metallic bodies simultaneously. If desired, a collection of mutually different sources can be manufactured, stored in an in situ "library" (rack, cassette, carrousel) within the X-ray imaging apparatus, and (automatically) retrieved/deployed at will, thereby allowing imaging using a variety of different (customized) source configurations.

In the embodiment just described, the combination of supporting material+suspended bodies essentially acts as a sort of "spatial filter", whose (fixed) configuration/patterning will cause localized generation of X-rays at some locations (the coordinates of the metallic bodies) with intervening areas of insignificant X-ray generation (in the supporting low-Z material). In an alternative/supplemental embodiment to that set forth in the preceding paragraph—which provides flexible/"programmable" configuration possibilities—the employed source comprises an array of individually selectable FEGs (Field Emission Guns; which may be of cold-cathode or Schottky type, for example). Such arrays are, for example, known from electron-beam lithography, where they are employed to produce a grid of electron beams that are used to simultaneously write a corresponding grid of pattern subsections on a semiconductor substrate. In the current invention, however:

- Rather than (always) firing all the FEGs in the array, one can instead elect to switch on only a chosen subset of FEGs that are located at pre-selected array coordinates (cell positions);
- The FEGs are ultimately used to produce X-rays. This can, for example, be realized by:
  - Providing each FEG with its own mini metal target, which converts to an X-ray source when bombarded by its FEG;
  - Arranging a thin metallic film directly in front of the FEG array, which film then undergoes (highly) localized bombardment when a FEG at a given coordinate position is fired, whereby a localized area of the film at those coordinates will become an X-ray source.

Selective switching/firing of FEGs may, for example, be achieved by shuttering/de-shuttering them using beam blankers, or by using deflectors to deflect their beams into/out of a reference direction.

Note that, in embodiments in which the component sources are fired sequentially rather than simultaneously, one might ask why the camera doesn't make a separate image for each firing event rather than acquiring an integrated/composite image. One reason is that the (relatively slow) capture rate of the employed camera may not be able to keep pace with a (relatively fast) firing rate of the component sources (chosen so as to mitigate thermal issues in the source, for example).

The invention will now be elucidated in more detail on the basis of exemplary embodiments and the accompanying schematic drawings, in which:

FIG. 1 renders a perspective view of a specimen undergoing X-ray imaging, and serves to explain certain geometric aspects of this procedure.

FIG. 2A renders a longitudinal cross-sectional elevation of a particular embodiment of the present invention.

FIG. 2B shows part of the subject of FIG. 2A, viewed head-on.

FIGS. 4A, 4B and 4C show X-ray imagery of a test specimen, together with the employed source configuration, for prior-art and inventive embodiments.

Figure 6B:
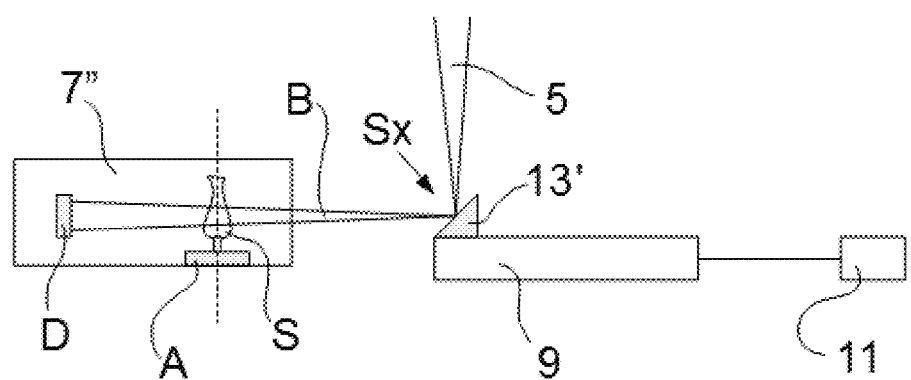
Figure 6A:
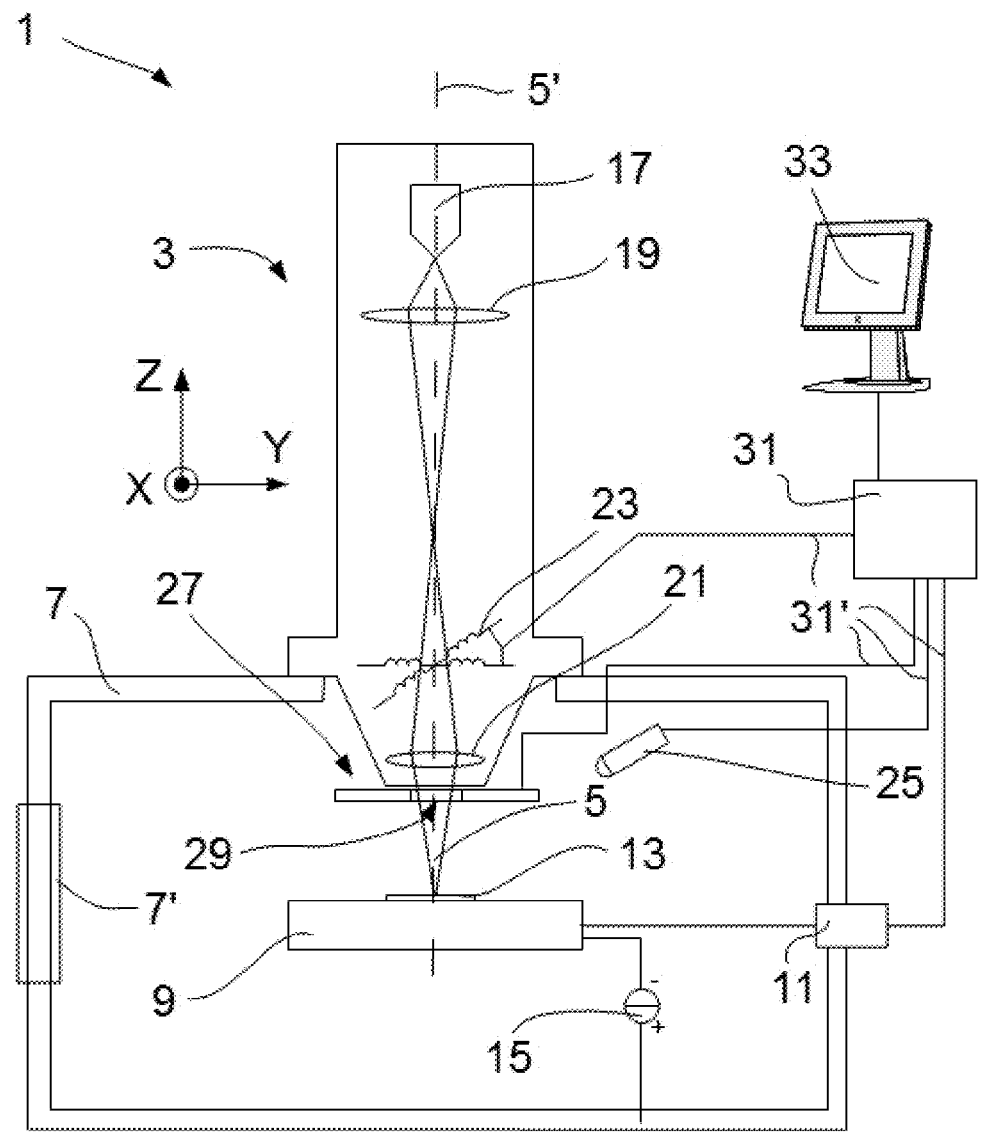

FIG. 6A renders a longitudinal cross-sectional elevation of a particular type of CPM in which an embodiment of the current invention can be carried out using a CT module.

FIG. 6B illustrates a CT module suitable for use in a CPM such as that shown in FIG. 6A.

EMBODIMENT 1

Figure 1:
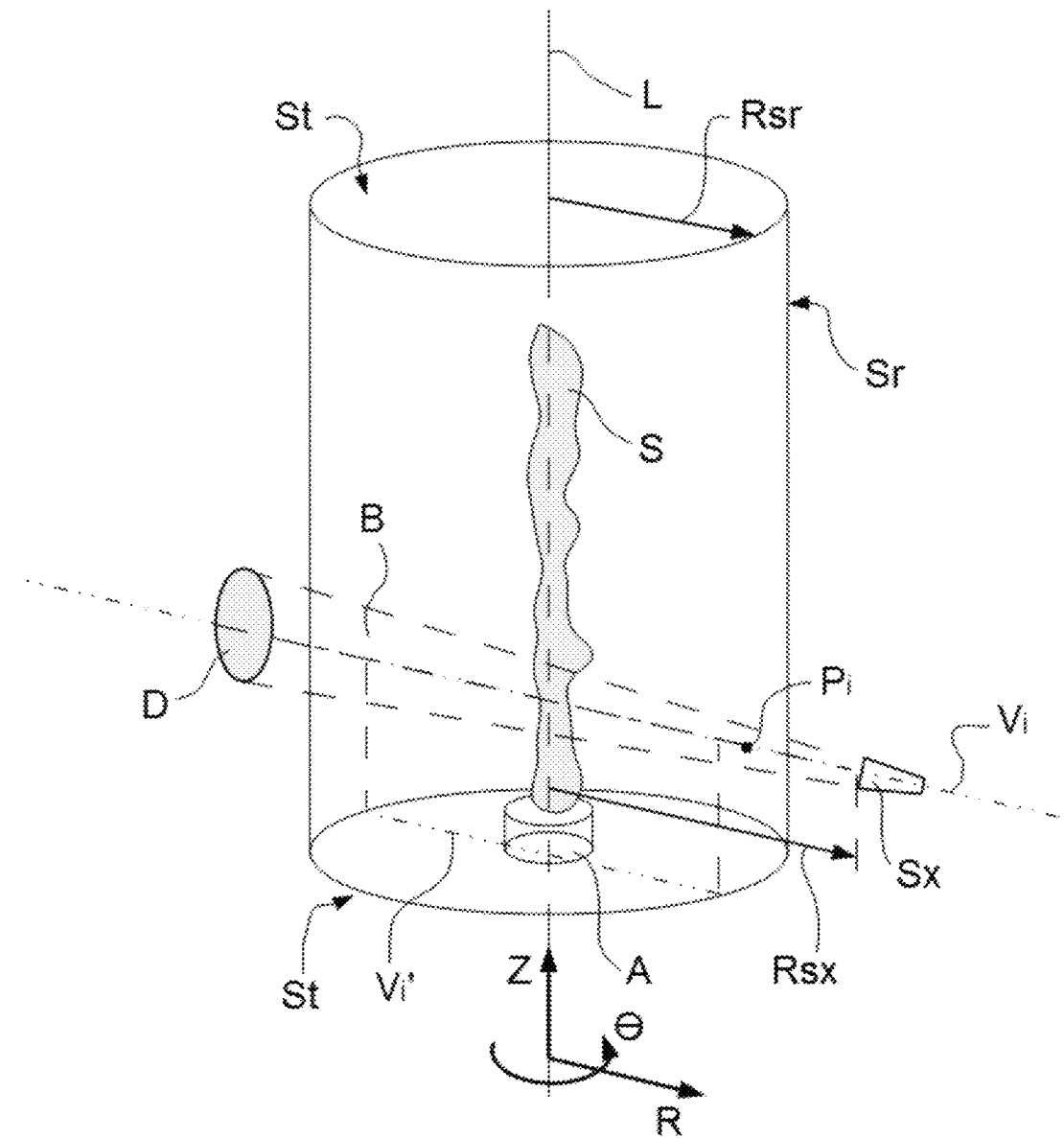

FIG. 1 renders a perspective view of a specimen S undergoing X-ray imaging, and serves to explain certain geometric aspects of such a procedure. In this particular case, the specimen S (which may be macroscopic, micron-scale, or nanometer-scale, for example) is elongate in form, with an associated longitudinal axis L. A radiation source Sx produces a beam B of X-rays that propagates along an axis $V_i$, which may be regarded as a viewing axis or line of sight. As here illustrated, $V_i$ is substantially normal to longitudinal axis L. Having traversed a portion of the specimen S, the beam B impinges upon a (diametrically opposed) camera (detector) D, which may, for example, be a CCD camera, CMOS camera, hybrid photon-counting camera, or other suitable camera. The beam B may be regarded as being (for example) cone- or fan-shaped, depending on the effective shape that the camera D "presents" to the source Sx. The camera D forms an electronic image of said portion of the specimen S, which can be stored in an electronic memory.

If one wants to perform a tomographic imaging series, then the procedure in the preceding paragraph can be repeated for a series of different viewing axes $V_i$, allowing the specimen S to be viewed along different lines of sight; thereafter, the various images acquired in this manner are used as input to a mathematical reconstruction procedure to produce a tomogram. The various viewing axes $V_i$ are achieved by employing a stage apparatus to produce relative motion between the source Sx and specimen S, e.g. by producing translational/rotational motion of the source Sx/camera D and/or the specimen S in a pre-determined way. Such stage apparatus may, for example, comprise one or more linear motors, piezoelectric actuators, stepper motors, voice coil motors, pneumatic/hydraulic actuators, etc., and can readily be tailored by the skilled artisan to suit the needs of a given setup. In the specific embodiment depicted here, stage apparatus A can translate/rotate specimen S relative to source Sx/camera D.

Also shown in the Figure is a virtual reference surface Sr, which, in this case, is a cylindrical surface whose cylindrical axis coincides with longitudinal axis L. This reference surface Sr has a radius Rsr, chosen to be less than or equal to the distance Rsx of the source Sx from the axis L. The viewing axis $V_i$ intersects this reference surface Sr at intersection point $P_i$. Note that, if viewing axis $V_i$ is projected linearly along L, it will coincide with a diameter of a virtual disc-shaped terminal surface St at butt ends of the surface Sr. Associated with the reference surface Sr is a cylindrical coordinate system (R, θ, Z). The set $\{P_i\}$ of intersection points $P_i$ corresponding to the abovementioned series of viewing axes $V_i$ can be regarded as representing a "data acquisition locus", such as the circular or helical scanning path referred to above, or the lattice-like locus set forth in aforementioned patent application EP15181202.1, for example.

EMBODIMENT 2

In the prior art, the source Sx shown in FIG. 1 (for example) will be a simple, unitary source. In contrast, in the current invention, the employed source Sx has a compound structure, and comprises a cluster of component sources (sub-sources). An embodiment of such a situation is illustrated in FIG. 2, in which:
 The source Sx comprises a body (foil, F) of supporting material Ss in which the component sources Sc are suspended/incorporated as discrete metallic bodies;
 Component sources Sc are caused to emit X-rays by irradiating them with a charged-particle beam 5.
In this particular example, the following non-limiting choices have been made:
 Bombarding beam 5 is wide enough to irradiate several of the component sources Sc simultaneously. This does not have to be the case, and one could instead focus beam 5 more sharply, so that it only irradiates one component source Sc at a time.
 The foil (body) F is canted (at approximately 45°) with respect to the incoming beam 5, and the source/camera (not depicted; see FIG. 6B, for example) are located off to the left of the Figure. This does not necessarily have to be the case, and one could instead arrange the foil F to be (more) normal to the beam 5, for example.
The foil F will typically comprise a low-Z material such as carbon, whereas the metallic bodies Sc will typically comprise a high-Z material such as gold, for instance. In a non-limiting example, the following choices can be made:
 Thickness of film F: 200-500 nm.
 Component sources Sc embodied as spheroids, with diameter d≈100 nm.
 The areal distribution of component sources Sc within the film F (as presented to the incoming beam 5) is (pseudo-)random (see FIG. 2B), so that the separation s of any given neighboring pair of spheroids Sc is variable; however, as here embodied, s will (on average) be of the same order of magnitude as d.
FIG. 2B shows the film F of FIG. 2A, but now viewed "face-on" parallel to the direction of normal N in FIG. 2A. The distribution of component sources Sc is seen to be non-regular; however, this does not have to be the case, and one could instead opt for a regular/repetitive distribution (similar to that illustrated in the upper portion of FIG. 5A, for example). In FIG. 2B, a virtual dashed circle C just encapsulates/surrounds the cluster of component sources Sc. A diameter (not shown) of this circle C will typically subtend a small angle θ at a (non-depicted) barycenter Cs of the (portion of the) specimen S being irradiated by the beam B (see FIG. 2A and FIG. 1), e.g. an angle θ≤ca. 1°.

Figure 2A:
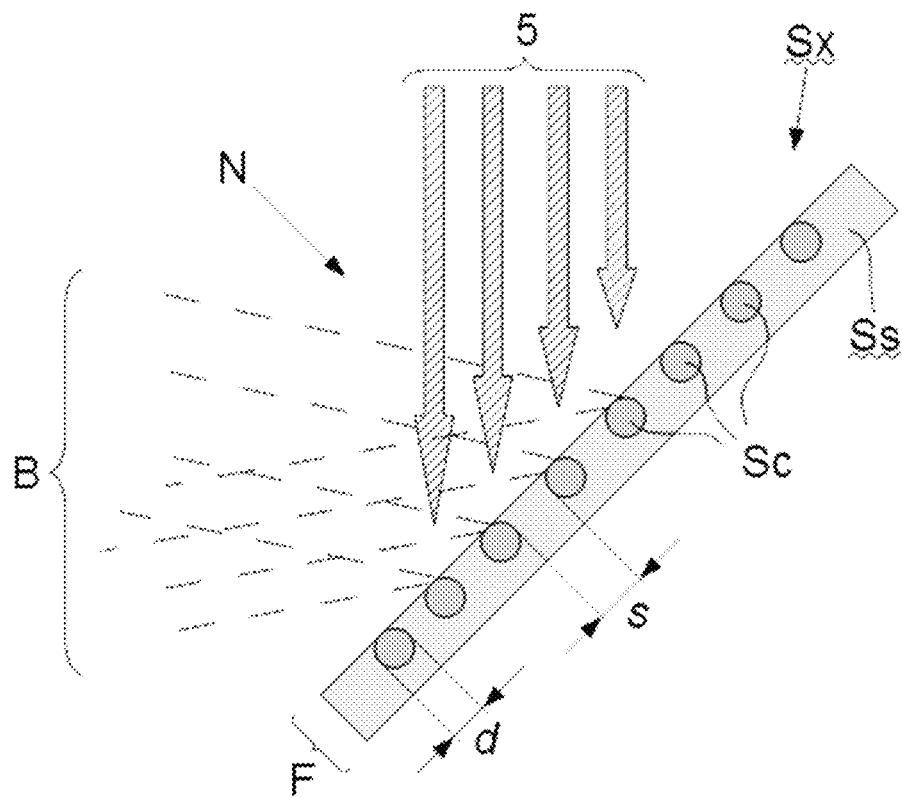
Figure 2B:
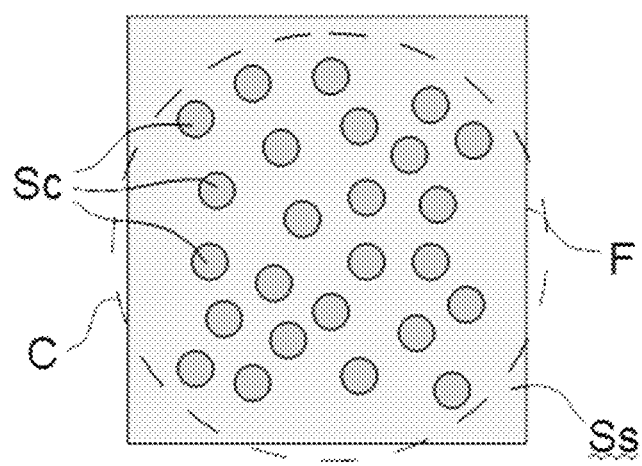

Considering the axis $V_i$ of FIG. 1, the various component sources Sc of FIGS. 2A, 2B will each have a different (angular) position relative to $V_i$; consequently, the sub-images (at camera D) associated with the various sub-sources Sc will be positionally shifted relative to one another, so that a composite/integrated image captured by detector D will be a convoluted, "blurry mess" in which these various sub-images partially overlap (see lower portion of FIG. 4B, for example). The mathematical deconvolution technique of the present invention deconvolves this composite image, producing a crisp, high-resolution result (see lower portion of FIG. 4C, for example).

Figure 2C:
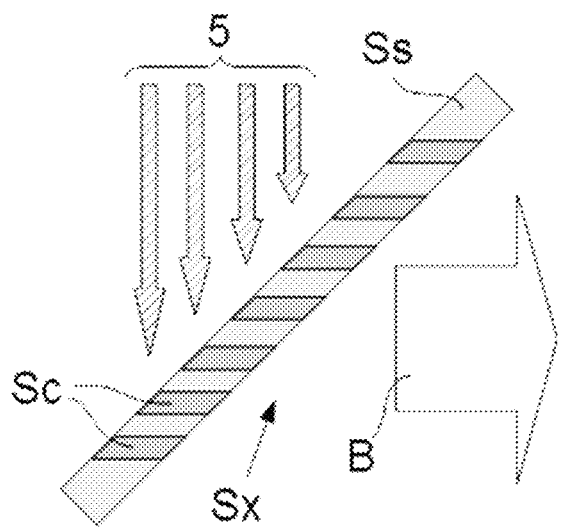
FIGS. 2C and 2D depict variants of the basic type of embodiment shown in FIG. 2A.
Figure 2D:
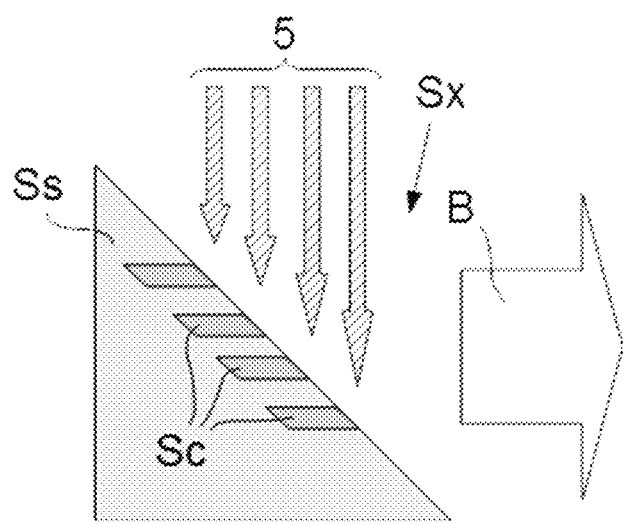

FIGS. 2C and 2D depict possible variants of the inventive set-up shown in FIG. 2A, whereby:
 In FIG. 2C, the component sources Sc are embodied as elongate metallic bodies (e.g. cylinders, rods) that (for instance) extend substantially parallel to the direction in which the specimen S is located (off to the right of the Figure in this case). These elongate component sources Sc may, for example, have a (width-to-length) aspect ratio of 1:5.
 In Figure D, the foil F of FIG. 2A (and FIG. 2C) is replaced by a bulk body (e.g. a block) of supporting material Ss, with the component sources Sc (which, in this case, are elongate, just as in FIG. 2C) being embedded in a (canted) surface of the body that is exposed to the bombarding beam 5. Such an embodiment has (for example) improved heat conduction/robustness as compared to a foil.
With regard to the discussion above, the following non-limiting data can be mentioned:
 Typical current densities can be of the order of ca. 10-100 $\mu A/\mu m^2$.
 If one chooses a smallest focused spot size of the bombarding electron beam to be 1 μm, for example, then a current density of 20 $\mu A/\mu m^2$ can be attained. For component sources of size ca. 100 nm, the effective (intercepted) current per component source will then be ca. 155 nA.
 Assuming a typical X-ray yield of $10^{-3}$ photons/electron (emitted in 4π sr), this will correspond to ca. $7.8 \times 10^7$ photons/sr s per component source (sr=steradian).
 If, for example, there are 20 such component sources within an area of 1 $\mu m^2$ on the source surface, then this will result in a total X-ray emission of ca. $1.6 \times 10^9$ photons/sr s. If a camera pixel captures ca. 10$ sr, then this will correspond to an X-ray yield of ca. 16 photons/s.

EMBODIMENT 3

Figure 3:
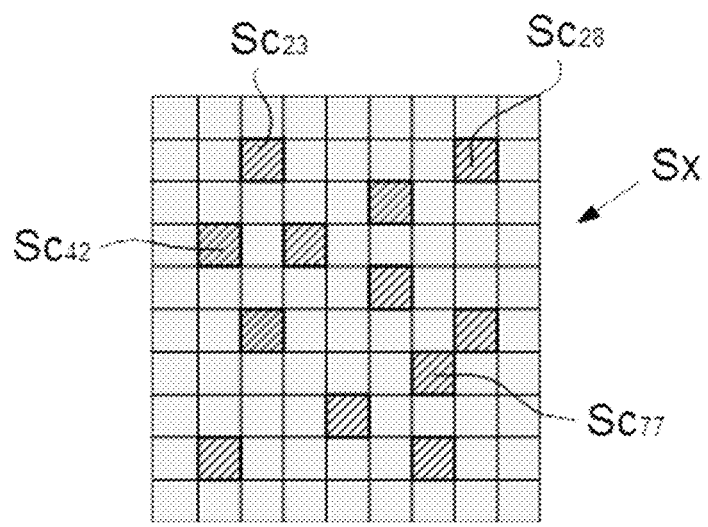
FIG. 3 shows an alternative type of embodiment to that illustrated in FIG. 2B.

As an alternative to the set-up shown in FIG. 2A, one could use an arrangement such as that depicted in FIG. 3, which illustrates (face-on) an array of individually selectable FEGs; in such a construct, the individual FEGs act as the component sources Sc of the present invention, and the array of FEGs can be considered as the composite source Sx. In this particular scenario, the FEGs are arranged in an orthogonal array, in which a given FEG $Sc_{ij}$ can be labeled/addressed according to its (horizontal) row number i and (vertical) column number j in the array—so that, for example, FEG $Sc_{23}$ is located in row 2 and column 3; however, this does not have to be the case, and one could instead choose another array geometry, such as hexagonal/honeycomb or polar, for example. Regardless of the chosen array geometry/dimensions, the crux of the current embodiment is that various patterns/distributions of component sources Sc can be achieved at will by selectively activating/firing the FEGs at chosen coordinate/cell positions. As explained above, the electrons emerging from the activated FEGs can, for example, be used to produce X-rays using the following (non-depicted) means:

Each FEG has its own metallic mini-target, placed in the electron path;

A metallic foil is placed just in front of the array, and is locally irradiated by the electrons from a given FEG.

The skilled artisan will grasp these points, and be able to choose an implementation that suits the parameters/requirements of a given situation.

EMBODIMENT 4

FIGS. 4A, 4B and 4C show X-ray imagery of a test specimen, together with the employed X-ray source configuration, for prior-art and inventive embodiments. The specimen in this case is a mouse embryo (1.6 cm long). In each figure:

The top row/upper portion illustrates an employed source configuration;

The bottom row/lower portion illustrates an associated X-ray image.

More specifically:

FIG. 4A relates to the use of a single (non-compound) source, as employed in the prior art.

FIG. 4B shows a compound/composite source of a type as prescribed by the present invention; however, the associated integrated image has not been deconvolved, and is therefore very blurry.

FIG. 4C essentially shows the same situation as that in FIG. 4B, except in that the associated image has now been deconvolved in accordance with the present invention. It is immediately apparent how crisp and detailed this image is in relation to the corresponding images in FIGS. 4A and 4B. Note that the inventive source illustrated in FIGS. 4B and 4C has 49 component sources, in an essentially random areal distribution of dimensions ca. 1.9 µm×1.9 µm. Each component source has a size (width) of ca. 100 nm.

EMBODIMENT 5

Figure 5A:
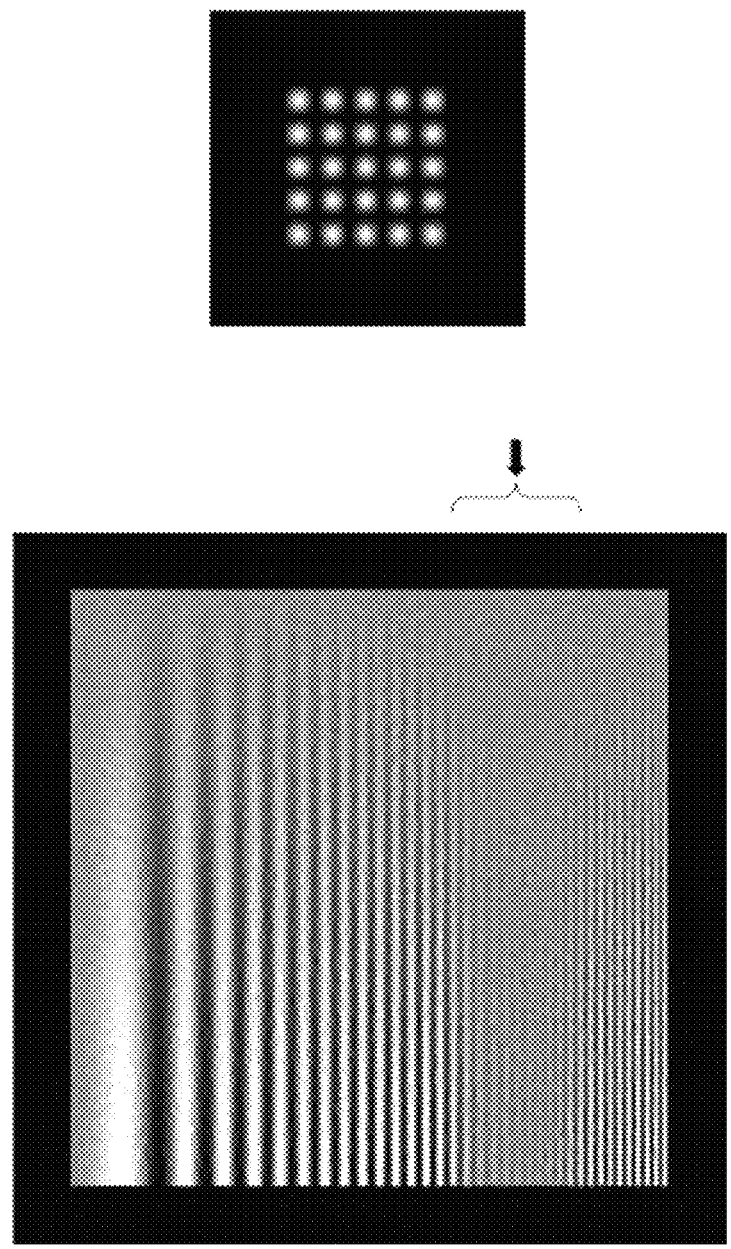
FIGS. 5A and 5B show X-ray imagery of a different test specimen, together with the employed source configuration, for particular embodiments of regular and non-regular distributions of component sources according to the present invention.
Figure 5B:
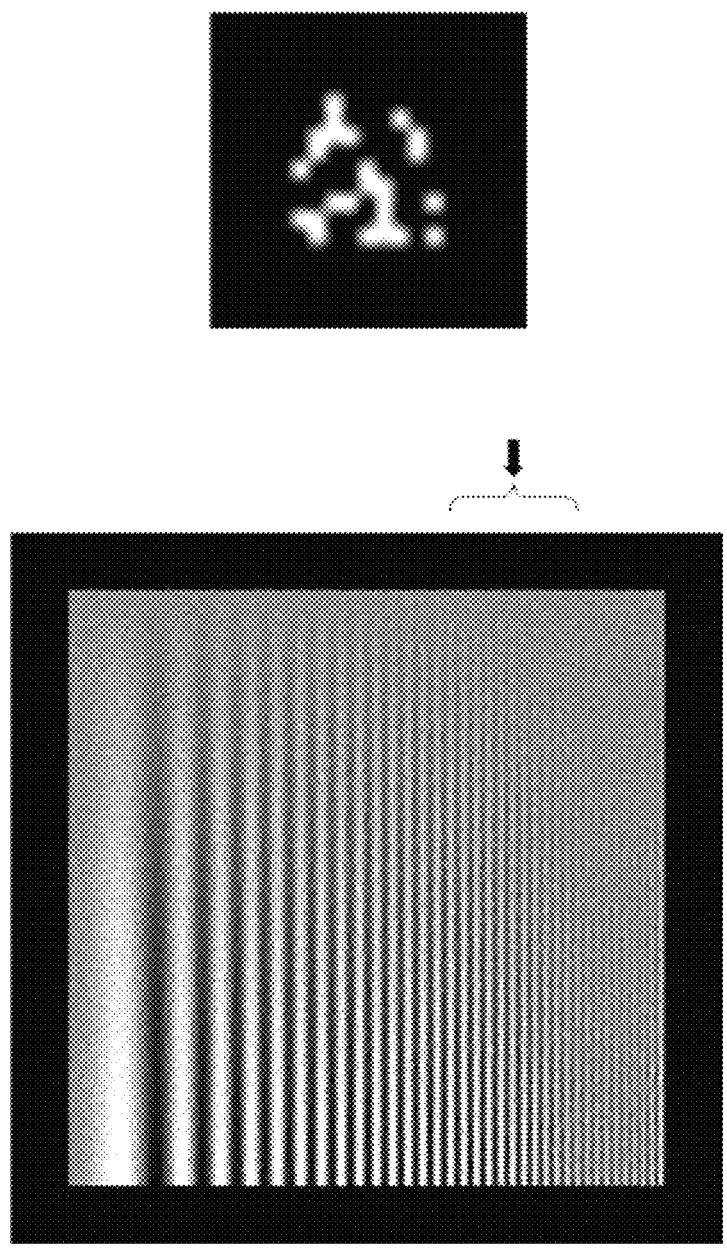

FIGS. 5A and 5B show X-ray imagery of a test specimen—together with the employed source configuration—for particular embodiments of regular and non-regular distributions of component sources according to the present invention. The specimen in this case is a grating pattern with a monotonically varying pitch, from coarse (left) to fine (right), with a spatial frequency of ca. 0.007 nm$^{-1}$ at the very right of the grating. As in the case of FIGS. 4A-4C:

The top row/upper portion illustrates an employed source configuration;

The bottom row/lower portion illustrates an associated X-ray image.

Note that:

In FIG. 5A, the employed composite source has a regular arrangement of component sources, which are located on the nodes of an orthogonal net. This arrangement has an intrinsic periodicity, which affects the Fourier spectrum of the corresponding image. In particular, the image comprises an associated zone (indicated using an arrow) in which there is suppressed contrast.

In FIG. 5B, the component sources of the composite source have an irregular/random areal arrangement, without the intrinsic periodicity of the grid-like array of FIG. 5A. This results in a flatter Fourier spectrum. As a result, the associated image is now free of the lower-contrast band that is prominent in the imagery of FIG. 5A. Note that the slight loss of contrast at the very right of FIG. 5B is an artifact effect, caused by the fact that the adopted Gaussian noise model in the employed IRLS deconvolution process was not perfectly representative of reality.

EMBODIMENT 6

FIG. 6A is a highly schematic depiction of an embodiment of a CPM 1 that can be used in conjunction with the present invention; more specifically, it shows an embodiment of a SEM—though, in the context of the current invention, it could just as validly be an ion-based microscope, for example, or a TEM, for instance. The microscope 1 comprises a particle-optical column/illuminator 3, which produces a beam 5 of charged particles (in this case, an electron beam) that propagates along a particle-optical axis 5'. The particle-optical column 3 is mounted on a vacuum chamber 7, which comprises a specimen holder 9 and associated stage/actuator 11 for holding/positioning a specimen 13. The vacuum chamber 7 is evacuated using vacuum pumps (not depicted). With the aid of voltage source 15, the specimen holder 9, or at least the specimen 13, may, if desired, be biased (floated) to an electrical potential with respect to ground.

The particle-optical column 3 comprises an electron source 17 (such as a Schottky emitter), (electrostatic/magnetic) lenses 19, 21 (in general, more complex in structure than the schematic depiction here) to focus the electron beam 5 onto the specimen 13, and a deflection unit 23 to perform beam deflection/scanning of the beam 5. When the beam 5 impinges on/is scanned across the specimen 13, it will precipitate emission of various types of "stimulated" radiation, such as backscattered electrons, secondary electrons, X-rays and cathodoluminescence (infra-red, visible and/or ultra-violet photons); one or more of these radiation types can then be sensed/recorded using one or more detectors, which may form an image, spectrum, diffractogram, etc., typically by assembling a "map" (or "matrix") of detector output as a function of scan position on the specimen. The present Figure shows two such detectors, 25, 27, which may, for example, be embodied as follows:

Detector 25 may, for example, be an electron detector (such as an Solid State Photo-Multiplier), X-ray detector (such as an SDD or Si(Li) sensor) or a light detector (such as a photodiode).

Detector 27 is a segmented electron detector, comprising a plurality of independent detection segments (e.g. quadrants) disposed about a central aperture 29 (allowing passage of the beam 5). Such a detector can, for example, be used to investigate (the angular dependence of) a flux of output (secondary or backscattered) electrons emerging from the specimen 13.

These are just examples, and the skilled artisan will understand that other detector types, numbers and geometries/configurations are possible.

The microscope 1 further comprises a controller/computer processing unit 31 for controlling inter alia the lenses 19 and 21, the deflection unit 23, and detectors 25, 27, and displaying information gathered from the detectors 25, 27 on a display unit 33 (such as a flat panel display); such control occurs via control lines (buses) 31'. The controller 31 (or another controller) can additionally be used to perform various mathematical processing, such as combining, integrating, subtracting, false colouring, edge enhancing, and other processing known to the skilled artisan. In addition, automated recognition processes (e.g. as used for particle analysis) may be included in such processing.

Also depicted is a vacuum port 7', which may be opened so as to introduce/remove items (components, specimens) to/from the interior of vacuum chamber 7, or onto which, for example, an ancillary device/module may be mounted (not depicted). A microscope 1 may comprise a plurality of such ports 7', if desired.

If desired, the microscope 1 can also comprise an in situ CT module 7" as shown in FIG. 6B. In this figure, the CPM's specimen holder 9 has been provided with a metallic target 13', which is positioned (using actuator 11) so that electron beam 5 impinges upon it, thus producing Bremsstrahlung (and characteristic) X-rays in a variety of directions. The Figure shows a beam B of such X-rays that propagate to one side from target 13' (effective source Sx) into module 7", where they pass through a specimen S and impinge upon a detector (camera) D: compare to FIG. 1. The specimen S is mounted on a stage apparatus A that allows the specimen S to be positioned/moved (typically translated and rotated) relative to the source Sx. In the specific context of the current invention:

The target 13' may be a composite source Sx as illustrated in FIGS. 2A-2D, for example;

The mathematical deconvolution of the integrated image recorded by detector D may, for example, be performed using controller 31.

Such a CT module 7" may be permanently present (ab initio) in the vacuum enclosure 7, or it may be an add-on module that can be mounted (post-manufacture of the CPM 1) on/within a spare vacuum port 7', for example.

EMBODIMENT 7

Reconstruction Algorithms for a Compound/Composite Source (Patterned Source)

In the following, the imaging process is modeled using a convolution operation, where y is the measured image, h the point spread function kernel, x the unknown 'un-blurred' image and * the convolution operator:

$$y = h * x \quad (1)$$

In Bayesian terms, one can represent the probability of the sought image x given the known image y as $$P(x|y) = P(y|x)P(x) \quad (2)$$

Examples of likelihood functions P(y|x) that can be used include the following:

For imaging processes affected by Gaussian noise:

$$P(y \mid x) = \exp\left(-\frac{|y - h * x|^2}{\sigma^2}\right) \quad (3)$$

For Poisson processes:

$$P(y|x) = C\Pi_y (h*x)^y \exp(-h*x) \quad (4)$$

Typically, knowledge about the images to be reconstructed is modeled within the Prior term $P(x) = P(R(x))$ such that:

$$P(x|y) = P(y|x) \cdot P(R(x)) \quad (5)$$

Often, R(x) is a user-defined function that maximizes the prior probability for a desired intensity distribution. Also common is a choice of R(x) that imposes constraints on the distribution image gradients:

$$R(x) = -\alpha p(\nabla x) \quad (6)$$

Note that:

If $(z) = |z|^2$, one is assuming overall smooth images with derivatives near zero.

Another possible choice is $(z) = |z|^\mu$, where $\mu < 1$. In particular, the choice of $\mu = 0.8$ can been shown to give good results for the reconstruction of natural images by imposing a sparse distribution of image gradients. See, for example:

A. Levin, et al., Image and depth from a conventional camera with a coded aperture, ACM Transactions on Graphics (TOG) 28(3) (ACM), 2007.

Other choices for p include the Student-t distribution and scale mixtures of Gaussians.

The reconstruction process essentially consists of finding the most likely image x*:

$$x^* = \text{argmax}_x \{\log(P(y|x)P(x))\} \quad (7)$$

The iterative solution of (7) can, for example, be found using gradient-descent based techniques, such a quasi-Newton technique.

For the specific case of an image with Gaussian noise and using a sparse gradient prior term, the optimization problem reduces to:

$$x^* = \text{argmin}_x \left\{ \frac{|y - h * x|^2}{\sigma^2} + \alpha |\nabla x|^\mu \right\} \quad (8)$$

Any of the previously mentioned optimization techniques can be used. In particular the Iterative Re-weighted Least Square (IRLS) method proves effective in solving (8). It is to be noted that, in (7) and (8), one assumes prior knowledge of the PSF kernel h, which encodes the way the ideal image pixels are mixed in the blurred observed image. Such knowledge of h can be obtained by imaging the source pattern in the absence of the sample, from theoretical optical modeling, or from simulations, for example. If one cannot discern h beforehand, then one can alternately solve for both variables x and h in a so-called blind reconstruction problem. In this case (8) will be reformulated as:

$$x^*, h^* = \text{argmin}_{x,h} \left\{ \frac{|y - h * x|^2}{\sigma^2} + \alpha |\nabla x|^\mu \right\} \quad (9)$$

Additionally, if the kernel h is characterized with high-resolution—e.g. using measurements, theoretical knowledge or simulation—one can recover a super-resolved image from the observed image using compressive sensing techniques. In this task, one represents the convolution imaging process of (1) by a matrix-vector multiplication, by serializing x and y while representing the kernel h by the corresponding matrix operator H, leading to:

$$y = D \cdot H \cdot x \quad (10)$$

where D is a down-sampling matrix operator (e.g. sampling every other image pixel). In the well-known compressive sensing approach, the reconstruction task can be cast as a constrained ti-minimization problem:

$$\min_x \|x\|_1 \quad (11)$$

-continued $$such\ that\ y = D \cdot H \cdot x$$

Various methods can be employed to solve for (11), such as Linear Programming, Basis Pursuit De-noising, Orthogonal Matching Pursuit and Iterated Hard Thresholding, for example.

The invention claimed is:

1. A method of imaging a specimen using an X-ray imaging apparatus, comprising:
    providing the specimen on a specimen holder;
    directing a flux of X-rays from a source through the specimen and onto an X-ray camera,
    embodying the source as a cluster of component sources, with a confined angular span relative to the specimen;
    using said camera to record a cumulative, composite image from said component sources; and
    mathematically deconvolving said composite image, wherein
    the source comprises a body of supporting material in which each of the cluster of the component sources are incorporated as discrete metallic bodies, and wherein the discrete metallic bodies are incorporated into the body of the supporting material in an irregular areal distribution such that a separation between any given neighboring pair of discrete metallic bodies is variable; and
    component sources are caused to emit X-rays by irradiating them with a charged-particle beam.

2. A method according to claim 1, wherein said deconvolution is performed using an iterative re-weighted convergence technique employing a Point Spread Function kernel for said cluster of component sources.

3. A method according to claim 2, wherein at least some of said component sources are deployed sequentially to image the specimen.

4. A method according to claim 2, wherein at least some of said component sources are deployed simultaneously to image the specimen.

5. A method according to claim 2, wherein said angular distribution is non-regular.

6. A method according to claim 1, wherein at least some of said component sources are deployed simultaneously to image the specimen.

7. A method according to claim 6, wherein said angular distribution is non-regular.

8. A method according to claim 1, wherein said angular distribution is non-regular.

9. A method according to claim 1, wherein said angular span $\theta$ relative to the specimen satisfies $\theta<10°$.

10. A method according to claim 1, wherein said source comprises an array of individually selectable FEGs.

11. A method according to claim 1, wherein the deconvolved composite image is employed as an input component image in a tomographic imaging procedure.

12. A method according to claim 1, wherein said angular span $\theta$ relative to the specimen satisfies $\theta<5°$.

13. A method according to claim 1, wherein said angular span $\theta$ relative to the specimen satisfies $\theta<1°$.

14. A method according to claim 1, wherein the average separation between any given neighboring pair of discrete metallic bodies is of the same order of magnitude as the diameter of the discrete metallic bodies.

15. An X-ray imaging apparatus comprising:
    a specimen holder, for holding a specimen;
    an X-ray source, for directing a flux of X-rays through the specimen and onto an X-ray camera; and
    an automatic controller, for controlling at least part of the operation of the apparatus,
    wherein the source is embodied as a cluster of component sources incorporated as discrete metallic bodies within a body of supporting material, the discrete metallic bodies having a confined angular span relative to the specimen holder and having an irregular areal distribution within the body of the supporting material such that a separation between any given neighboring pair of discrete metallic bodies is variable; and
    said controller is configured to:
        use said camera to record a cumulative, composite image from said component sources;
        perform a mathematical deconvolution procedure on said composite image.

16. An X-ray imaging apparatus according to claim 15, wherein said controller is configured to performed said deconvolution using an iterative re-weighted convergence technique employing a Point Spread Function kernel for said cluster of component sources.

17. A charged-particle microscope comprising an X-ray imaging apparatus as claimed in claim 16.

18. A charged-particle microscope comprising an X-ray imaging apparatus as claimed in claim 15.

19. A method of imaging a specimen using an X-ray apparatus, comprising:
    directing a flux of X-rays from a cluster of component sources incorporated as discrete metallic bodies within a body of supporting material and having a confined angular span relative to the specimen through the specimen and onto an X-ray camera, wherein the discrete metallic bodies are incorporated into the body of the supporting material in an irregular areal distribution such that a separation between any given neighboring pair of discrete metallic bodies is variable;
    recording a cumulative, composite image from said component sources; and
    forming an image of the specimen by mathematically deconvolving said composite image.

* * * * *